(12) United States Patent
Chang et al.

(10) Patent No.: US 8,974,770 B2
(45) Date of Patent: Mar. 10, 2015

(54) METHOD FOR FORMING NANO-BUBBLE

(75) Inventors: Walter H. Chang, Tao-Yuan (TW);
Cheng-An Lin, Tao-Yuan (TW);
Chih-Hsien Lee, Tao-Yuan (TW);
Chih-Kuang Yeh, Tao-Yuan (TW)

(73) Assignee: Chung Yuan Christian University, Tao-Yuan (TW)

(*) Notice: Subject to any disclaimer, the term of this patent is extended or adjusted under 35 U.S.C. 154(b) by 365 days.

(21) Appl. No.: 12/423,956

(22) Filed: Apr. 15, 2009

(65) Prior Publication Data

US 2010/0080759 A1 Apr. 1, 2010

Related U.S. Application Data

(60) Provisional application No. 61/100,931, filed on Sep. 29, 2008.

(51) Int. Cl.
| | | |
|---|---|---|
| *A61K 49/18* | (2006.01) | |
| *A61K 49/22* | (2006.01) | |
| *A61K 47/30* | (2006.01) | |
| *B82Y 5/00* | (2011.01) | |

(52) U.S. Cl.
CPC ............ *A61K 49/223* (2013.01); *B82Y 5/00* (2013.01); *Y10S 977/906* (2013.01); *Y10S 977/929* (2013.01)
USPC .......... 424/9.52; 977/906; 977/929; 427/2.12

(58) Field of Classification Search
None
See application file for complete search history.

(56) References Cited

U.S. PATENT DOCUMENTS

| | | | |
|---|---|---|---|
| 2006/0140865 A1* | 6/2006 | Chang et al. ................... | 424/9.6 |
| 2007/0189972 A1* | 8/2007 | Chiba et al. ................... | 424/9.52 |
| 2008/0181853 A1* | 7/2008 | Ottoboni et al. ............. | 424/9.52 |

OTHER PUBLICATIONS

Dissolution from Collins English Dictionary.*
"Cleaners Waxes and Polishes Acid Cleaning", http://www.chemical-supermarket.com/Aqua-Regia-(aka-Nitrohydrochloric-Acid)-c172.html.*
Balcerzak"Sample Digestion Methods for the Determination of Traces of Precious Metals by Spectrometic Techniques", Analytical Sciences, 2002, pp. 737-750.*
Yee et al. "Novel One Phase Synthesis of Thiol Functionalized Gold Palladium and Iridium Nanoparticles Using Superhydride" Langmuir, 15, 1999, pp. 3486-3491.*
Rao et al. "Chemistry changes with size", Chemistry A European Journal, 8(1), 2002, pp. 28-35.*
"Cleaners Waxes and Polishes Acid Cleaning", http://www.chemical-supermarket.com/Aqua-Regia-(aka-Nitrohydrochloric-Acid)-c172.html.*
Newman et al. "The Effect of Aniline Concentration in the Liand Exchange Reaction with Citrate-Stabilized Gold Nanoparticles", Langmuir, 2009, pp. 8993-8998.*
Xu et al. "Synthesis on Utilization of Monodisperse Hollow Polymeric Particles in Photonic Cyrstals" JACS, 126, 2004, pp. 7940-7945.*
http://dictionary.reference.com/browse/dialysis; dictionary.com.
http://www.merriam-webster.com/dictionary/dialysis; merriam-webster.
http://en.wikipedia.org/wiki/Dialysis; Wikipedia; Jul. 17, 2012.
http://en.wikipedia.org/wiki/Osmotic_pressure; Wikipedia; Aug. 4, 2012.
http://dictionary.reference.com/browse/osmotic+pressure; dictionary.com.
http://www.merriam-webster.com/dictionary/osmotic+pressure; merriam-webster.

* cited by examiner

*Primary Examiner* — Kortney L Klinkel
*Assistant Examiner* — Melissa Javier
(74) *Attorney, Agent, or Firm* — WPAT, PC; Justin King

(57) ABSTRACT

The present invention discloses a method for forming a nano-bubble. The forming method is different from the oil-water emulsion reaction in the prior art. The method comprises: taking an inorganic particle as a nucleus and performing a polymer coating process to coat at least one first polymer on the surface of the nucleus to form an organic/inorganic composite particle; then removing the nucleus of the organic/inorganic composite particle by way of the dissolution of a first solvent to form an impregnated nano-particle; performing a freeze-drying process to remove the first solvent to have the impregnated nano-particle form a hollow nano-particle; and finally dissolving the hollow nano-particle in a second solvent to form the nano-bubble.

10 Claims, 3 Drawing Sheets

METHOD FOR FORMING NANO-BUBBLE

BACKGROUND OF THE INVENTION

1. Field of the Invention

The present invention is generally related to a method for forming a nano-bubble, and more particularly to a method for forming a nano-bubble used in an ultrasound contrast agent.

2. Description of the Prior Art

An ultrasound contrast agent (UCA) is the substance to enhance image contrast in ultrasound imaging. Generally, it is micrometer-scaled encapsulating micro-bubbles injected into blood circulatory system via intravenous injection to enhance the reflection of the ultrasonic waves to thereby achieve the purpose of enhancing the resolution of ultrasound imaging.

After injected into veins, an ultrasound contrast agent (UCA) can change the ultrasonic characteristics of a tissue, such as backscatter coefficient, decay coefficient, sound velocity, and non-linear effect, to produce the imaging effect. The enhancement depends on the concentration and dimension of the ultrasound contrast agent and the frequency of ultrasonic radiation. The basic property of an ultrasound contrast agent is to enhance the backscatters of tissues to enhance the visibility and contrast of the ultrasonogram in ultrasound imaging. The non-linear effect produces harmonic generation with certain energy and the harmonic imaging technique can be used to measure the blood flow of a small vein and tissue perfusion and can suppress the noise generated by the motion of the tissue comprising no ultrasound contrast agent at the fundamental frequency. Thus, the signal-to-noise ratio can be greatly enhanced.

The research and application on the ultrasound contrast agent can be traced back to the initial observation of the contrast effect of a cloud of echoes after the intracardiac injection of saline in 1968 by Gramiak et al. In the late 80's, the ultrasonic tissue characterization has certain difficulties due to similar ultrasonic characteristics between some tissues even though these tissues are pathologically different. Thus, the ultrasound contrast agent that enhances the echogenicity of tissues and blood has drawn great attention.

The generation of the contrast agent is classified according to the type of gas filled in micro-bubbles where the first-generation contrast agent is mainly filled with air that is encapsulated by polymers like albumin or galactose; and the second-generation contrast agent is filled with high-density inert gas that is encapsulated by a soft thin membrane. Compared to the second-generation contrast agent, the membrane of the first-generation contrast agent is thicker and less elasticity and the filled gas is apt to dissolve in water and thus the micro-bubbles of the first-generation contrast agent tends to be broken and has a short lifetime. Therefore, the time for observation and diagnosis in the clinical application is limited. However, the diameter of the micro-bubble of the second-generation contrast agent is reduced to about 2-5 μm and the micro-bubble has longer stable time. Thus, the second-generation contrast agent has better vibration and backscatter characteristics.

In the past few years, the ultrasound contrast agent has been widely utilized in ultrasound therapy. Since the micro-bubbles in the ultrasound contrast agent can enhance cavitation effect to promote ultrasonic bio-effect. Therefore, the research of the ultrasound contrast agent on the direction of therapy like ultrasound thrombolysis, ultrasound-mediated gene delivery, and high intensity focused ultrasound (HIFU) has been taken off. Since the application area of the ultrasound contrast agent is continually expanded, the application value is greatly promoted. Therefore, it is important for the industry to continually develop an ultrasound contrast agent having high stability, controlled dimension, biodegradability, and biocompatibility.

SUMMARY OF THE INVENTION

In light of the above background, in order to meet the requirements of the industry, the present invention provides a method for forming a nano-bubble.

The characteristic of the present invention is to provide a method for forming a nano-bubble. The forming method is different from the oil-water emulsion reaction in the prior art. The method comprises: taking an inorganic particle as a nucleus and coating at least one first polymer on the surface of the nucleus to form an organic/inorganic composite particle; then removing the nucleus of the organic/inorganic composite particle by way of the dissolution of a first solvent to form an impregnated nano-particle; performing a freeze-drying process to remove the first solvent to have the impregnated nano-particle form a hollow nano-particle; and finally dissolving the hollow nano-particle in a second solvent to form the nano-bubble.

The nano-bubble can be utilized in the following fields: ultrasound contrast agent, drug carrier, gene carrier, clinical diagnosis and clinical therapy.

DESCRIPTION OF THE PREFERRED EMBODIMENTS

Figure 1:
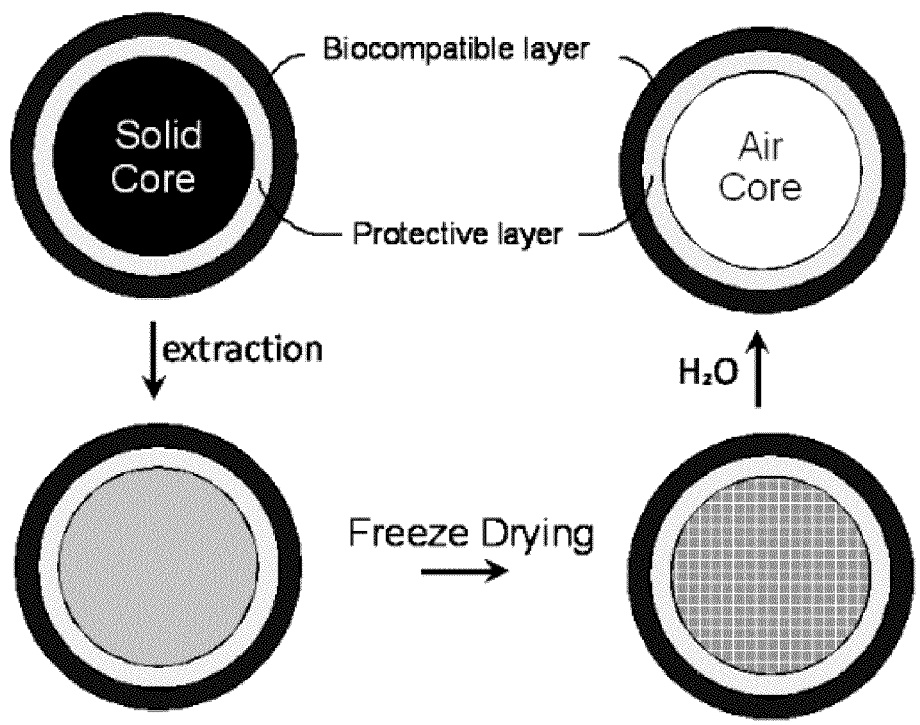
FIG. 1 is a schematic diagram illustrating the synthesis of the nano-bubble according to the embodiment of the invention.

What is probed into the invention is a method for forming a nano-bubble. Detail descriptions of the steps and elements will be provided in the following in order to make the invention thoroughly understood. Obviously, the application of the invention is not confined to specific details familiar to those who are skilled in the art. On the other hand, the common elements or steps that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One embodiment of the invention discloses a method for forming a nano-bubble. The forming method comprises the following steps. At first, an inorganic particle is taken as a nucleus and a polymer coating process to coat at least one first polymer on the surface of the nucleus to form an organic/inorganic composite particle is performed. The first polymer is (poly(isobutylene-alt-maleic anhydride)-graft-dodecylamine) or similar amphoteric polymer. Then, the organic/ inorganic composite particle is in contact with a first solvent and the nucleus of the organic/inorganic composite particle is removed via the dissolution of the first solvent to form an impregnated nano-particle. The inside of the impregnated nano-particle comprises the first solvent. Following that, a freeze-drying process to remove the first solvent to have the impregnated nano-particle form a hollow nano-particle is performed. The inside of the hollow nano-particle contains air. Furthermore, the hollow nano-particle is dissolved in a second solvent to form the nano-bubble.

In addition, the method for forming a nano-bubble further comprises a bioconjugation process to couple a second polymer having biocompatibility to the surface of the layer of the first polymer after performing the first polymer coating process. The second polymer is a molecule containing $NH_2$ moiety, such as 1-ethyl-3-dimethylaminopropyl carbodiimide (EDC).

The inorganic particle is one particle selected from the group consisting of the following: gold, silver, iron, and other inorganic nano-particles. The first solvent is aqua regia and the second solvent is pure water or various buffer solutions.

The particle diameter of the nano-bubble is 30 nm~10,000 nm and can be controlled by the dimension of the inorganic particle.

In a preferred example, the dissolution process further comprises applying a desired gas flow to the hollow nano-particle and dissolving the hollow nano-particle in the second solvent to form the nano-bubble containing the desired gas.

In another preferred example, the nano-bubble is vacuumed to remove the gas encapsulated in the nano-bubble and filled with a desired gas.

The gas contained in the nano-bubble is one gas selected from the group consisting of the following: fluoride gas, oxygen, nitrogen, argon, neon, xenon, and air, preferably, being $CF_4$, $C_2F_6$, $C_2F_4$, $C_3F_8$, $C_4F_8$, $C_4F_{10}$, $C_3F_6$, or $SF_6$. The nano-bubble according to the invention has the following application: ultrasound contrast agent, drug carrier, gene carrier, clinical diagnosis and clinical therapy. Besides, the nano-bubble is stable and the lifetime of the nano-bubble reaches 25~30 minutes. The lifetime of the nano-bubble means the duration that the nano-bubble can enhance the ultrasound echo signal while stimulated by a specific ultrasonic parameter.

Example

Nano-Bubble Synthetic Method (I) Synthesis of a Gold Nano-Particle

Preparing the following (a)~(e) solutions in advance:

(a) didodecyldimethylammonium bromide (DDAB) solution: using an electronic micro-balance to weight 4.63 g of DDAB (MW=462.63) and adding into 100 mL of toluene and then mixing by an oscillator until becoming homogeneous;

(b) gold chloride ($AuCl_3$) solution: using an electronic micro-balance to weight 0.15 g of $AuCl_3$ (MW=303.33) and adding into 20 mL of DDAB and then mixing by an oscillator until becoming homogeneous;

(c) dodecanic acid solution: using an electronic micro-balance to weight 1.376 g of dodecanic acid (MW=172.26) and adding into 80 mL of toluene and then mixing by an oscillator until becoming homogeneous;

(d) tetrabutylammonium bromide (TBAB) solution: using an electronic micro-balance to weight 0.15 g of TBAB (MW=257.31) and adding into 1.08 mL of DDAB and then mixing by an oscillator until becoming homogeneous; and (e) trioctylphosphine (TOP) solution: adding 0.17 mL of TOP into 3.8 mL of toluene and mixing by an oscillator until becoming homogeneous. The TBAB solution is the activator for synthesis of a gold nano-particle and thus it should be prepared just before synthesis.

A magnet is placed in a 20-mL sample flask. 2.5 mL of dodecanic acid solution and 1 mL of TBAB solution are taken and put in the 20-mL sample flask. The magnetic stir is used to stir the mixture by a proper rotating velocity. Then, 0.8 mL of $AuCl_3$ solution is added to react for 2 hours (firstly 10 μL is added and then 790 μL is quickly added). The 70° C. water bath is used to heat for 5 minutes. After the temperature reaches equilibrium, 40 μL of TOP solution is added to react for 5 minutes. Then, the magnet is taken out and methanol is added until the solution becomes cloudy. Furthermore, a centrifuge operated at a rotating velocity of 3000 rpm for 5 minutes is to remove small molecules and tiny impurities. The supernatant liquid is decanted. Chloroform is then used to dissolve the precipitated gold nano-particles. Finally, a centrifuge operated at a rotating velocity of 3000 rpm for 5 minutes is to remove larger gold nano-particles and larger impurities. The supernatant liquid is recovered in a clean sample flask.

(II) Polymer Coating

At first, the following solutions are prepared:

(a) polymer solution: taking 3.084 g (20 mmole) of poly (isobutylene-alt-maleic anhydride) (Mw~6,000) powder and placing in a round-bottom flask; dissolving 2.78 g (15 mmole) of dodecylamine in 100 mL of tetrahydrofuran (THF) solution; quickly mixing the dodecylamine solution and the poly (isobutylene-alt-maleic anhydride) powder to form a mixture solution; then setting the temperature of an evaporator to 60° C. and using a proper rotating velocity to react for 10 minutes to have the mixture solution become clear; setting the pressure to 200 mbar to react for 24 hours; after the solution is completely sucked, adding 25 mL of chloroform to dissolve the above synthesized polymer solution; where the monomer concentration of the polymer solution is 0.8M and each monomer unit comprises 25% of maleic anhydride groups and 75% of hydrophobic carbon chains;

(b) Sodium borate buffer (SBB): using an electronic micro-balance to weight 3.09 g of boric acid (MW=61.83 Da, 50 mM) and 19.07 g of sodium tetraborate decahydrate (MW=381.37 Da, 50 mM) and then dissolving in 1000 mL of secondary water and preserving at room temperature;

(c) 5×TBE buffer solution: using an electronic micro-balance to weight 54 g of tris-base and 27.5 g of boric acid to dissolve in 980 mL of secondary water and then adding 20 mL of ethylenediaminetetraacetic acid (EDTA, 0.5M, pH=8.0) and stirring by the magnet until the mixture becoming homogeneous; where the solution should be diluted to 0.5× before use;

(d) 2% agarose gel: placing a gel forming dish on the casting cell and setting an electrophoresis comb on the casting cell; using an electronic micro-balance to weight 2.4 g of agarose to place in a 250-mL Erlenmeyer flask and adding 120 mL of 0.5×TBE buffer solution; using a microwave oven to heat the mixture until agarose is completely dissolved and stirring evenly and, after the temperature becomes lower, slowly pouring the solution into the casting cell; then standing still until agarose becomes cold and coagulates; and finally pulling out the electrophoresis comb to place in the electrophoresis cell; and (e) Loading buffer solution: mixing glycerol with secondary water (v:v=1:10).

The absorption spectrum of the synthesized 6 nm gold nano-particle is measured by an absorption spectrometer and shows a 520 nm absorption peak for the 6 nm gold nano-particle. Beer's law: A=εbc is used to calculate the concentration of the gold nano-particle (molar absorption coefficient for the 6 nm gold nano-particle=2.905E7) where A is the absorbance, ε is the molar absorption coefficient (L/mol cm), b is the path length (cm) and c is the molar concentration (mol/L).

Assuming that the thickness of the organic molecule of the outer layer of the gold nano-particle is 1.1 nm, the total surface area of the gold nano-particle can be calculated. Assuming that 1 $nm^2$ needs 200 monomer units, the needed volume of the polymer solution can be calculated. At the beginning of the experiment, the calculated amount of the polymer solution and 5 mL of chloroform are well mixed in an eggplant-type flask. Then, the gold nano-particle solution is added and shaken by hand for 5 minutes to have the gold nano-particle solution and the polymer solution be well mixed. An evaporator (200 mbar, rotating speed 100 rpm) is used to suck the solution. After the solution is sucked completely, it is returned to atmospheric pressure and vacuumed again till reaching 1 mbar. After it is assured that the solution is sucked completely, 0.1N sodium hydroxide (NaOH) is added to quickly dissolve the polymer-modified gold nano-particle. Then, a 5 mL syringe is used to have the solution be filtered by a 0.2 μm filter. Furthermore, a 100 KDa molecular sieve is used to remove small molecules and the solvent is replaced by the sodium borate buffer (SBB) solution.

Agarose is used to purify the polymer-coated gold nano-particle. The polymer-coated gold nano-particle and the loading buffer solution (v:v=10:1) are mixed. 2% Agarose gel is placed in the TBE buffer solution of the electrophoresis cell to conduct purification (voltage 100V for 1 hour) to remove unreacted polymers. Then, the gold nano-particle is taken out from the agarose gel and placed in a dialyzing membrane. The gold nano-particle and the agarose gel are separated by the electric field in the 100V electrophoresis cell. The recovered sample is filtered by a 0.22 μm filter membrane and concentrated by a 100 KDa molecular sieve. The purified gold nano-particle is preserved in the sodium borate buffer (SBB) solution. Finally, the electrophoresis-purified polymer-coated gold nano-particle is centrifuged by a high-speed centrifuge operated at 5000 rpm for 20 minutes and then the supernatant liquid is removed and furthermore the sodium borate buffer (SBB) solution is used to dissolve the precipitated gold nano-particle (repeating 3 times).

(III) Biocompatible Layer Conjugation

The polymer-coated gold nano-particle is mixed with polyethyleneglycol (PEG) and 1-ethyl-3-dimethylaminopropyl carbodiimide (EDC) ([Au]/[PEG]=1/200, Au:PEG:EDC(v:v:v)=1:1:1) to react for 2 hours. Then, a 100 KDa filter tube (molecular weight cutoff; MWCO) is to remove unreacted PEG and the solution is concentrated to 1 μM and preserved in SBB (pH=9).

(IV)

Aqua regia is dripped into the sample processed by steps (II) and (III) until the solution becomes clear and transparent. A 100 KDa filter tube (molecular weight cutoff; MWCO) is used to replace aqua regia by SBB (pH=9) and then replace SBB by deionized water. Finally, a freeze-dryer is used to suck the solution until the sample becomes white solid. When the sample is to be stimulated by supersound, deionized water is added to dissolve the white solids. Thus, forming the nano-bubble is complete. The synthesis of the nano-bubble according to the embodiment of the invention is shown in FIG. 1. The gas in Air Core can be air and any inert gas, preferably $C_3F_8$, $C_4F_{10}$, and $SF_6$.

Figure 2:
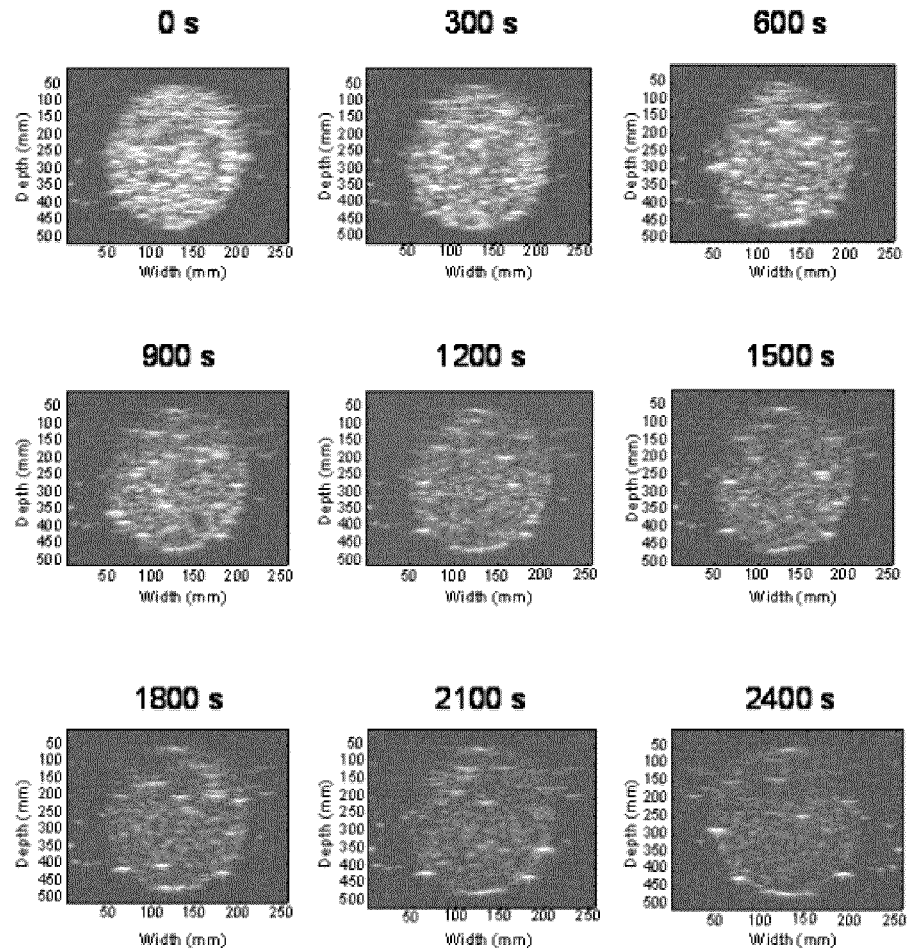
FIG. 2 is a schematic diagram illustrating the ultrasonogram of the nano-bubble according to the embodiment of the invention.
Figure 3:
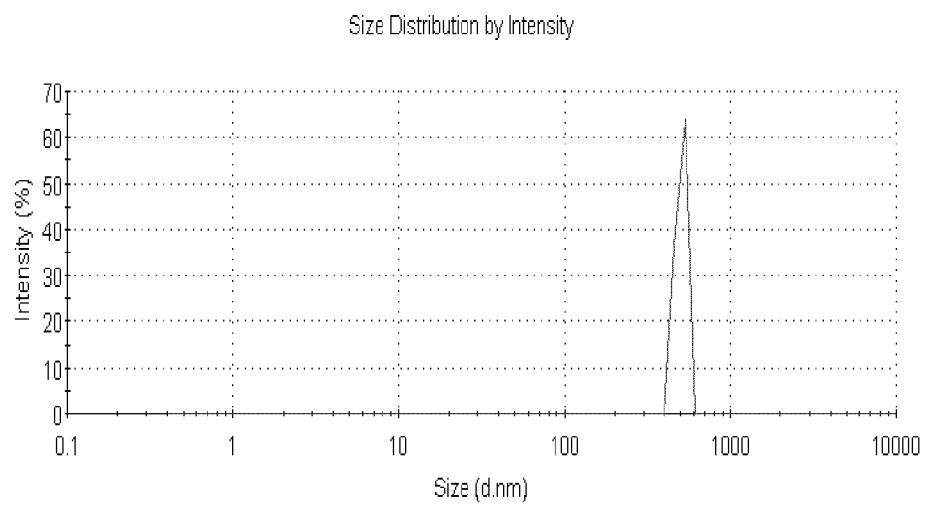
FIG. 3 is a schematic diagram illustrating the dynamic light scattering of the nano-bubble according to the embodiment of the invention.
Figure 4:
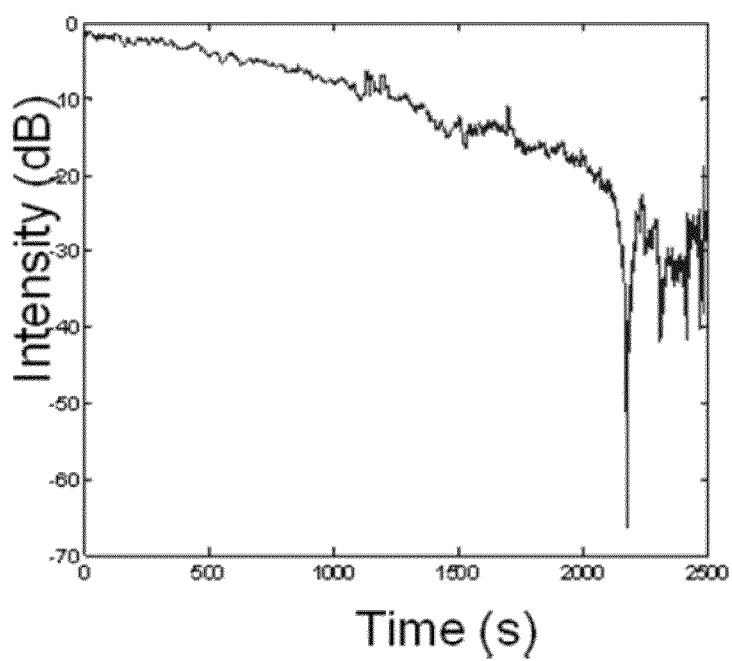
FIG. 4 is a lifetime measurement diagram of the nano-bubble according to the embodiment of the invention.

FIG. 2 shows the ultrasonogram of the nano-bubble while the nano-bubble is stimulated by ultrasound and the diameter of the nano-bubble is 10 μm. The dynamic light scattering (DLS) of the nano-bubble is measured, as shown in FIG. 3. Furthermore, the lifetime of the nano-bubble reaches 20 minutes, as shown in FIG. 4 where a 25 MHz probe is used in B-mode mapping by Panametric model 5900 pulser/receiver.

| Ultrasound parameters | |
| --- | --- |
| PRF: EXT BNC Gain: 40 dB | Energy: 32 μJ |
| Damping: 50 Ohm | High Pass: 10 MHz |
| Low Pass: 50 MHz | Lab View interface parameters |
| Sample Number: 512 | Sequence: 512 |
| Scan mode: B scan | PRF: 512 |
| Sample rate: 120M | Dynamic range: 1 V |
| Vectors: 4 mm | Speed: slow |
| Delay time: 0.0147 | Trig Type: positive |
| C scan depth: 1 mm | swept interval: 1 μm |

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for forming a nano-bubble, the method comprising:
    taking an inorganic particle as a nucleus and performing a polymer coating process to coat (poly(isobutylene-alt-maleic anhydride)-graft-dodecylamine) on the nucleus to form an organic/inorganic composite particle, wherein the inorganic particle is one particle selected from the group consisting of the following: gold, silver, and iron;
    dripping aqua regia into a solution containing said organic/inorganic composite particle to dissolve said nucleus;
    using a 100 KDa filter tube to replace aqua regia with sodium borate buffer (SBB), and then replacing the SBB with deionized water to remove the dissolved nucleus of the organic/inorganic composite particle, and forming an impregnated nano-particle impregnated with the deionized water;
    performing a freeze-drying process on the impregnated nano-particle to form a hollow nano-particle; and
    placing the hollow nano-particle into the deionized water to form the nano-bubble in the deionized water;
    wherein the nano-bubble has a particle diameter of 30-100 nm.

2. The method according to claim 1, wherein a particle diameter of the nano-bubble is controlled by a dimension of the inorganic particle.

3. The method according to claim 1, further comprising a step of performing a bioconjugation process to couple a second polymer having biocompatibility to surface of the (poly(isobutylene-alt-maleic anhydride)-graft-dodecylamine) after performing the polymer coating process.

4. The method according to claim 3, wherein the second polymer is a molecule containing $NH_2$ moiety.

5. The method according to claim 1, further comprising applying a desired gas flow to the hollow nano-particle to form the hollow nano-particle containing the desired gas.

6. The method according to claim 1, wherein the nanobubble is vacuumed and filled with a desired gas.

7. The method according to claim 1, wherein the nanobubble contains one gas selected from the group consisting of the following: fluoride gas, oxygen, nitrogen, argon, neon, xenon, and air.

8. The method according to claim 1, wherein the nanobubble contains one gas selected from the group consisting of the following: $CF_4$, $C_2F_6$, $C_2F_4$, $C_3F_8$, $C_4F_8$, $C_4F_{10}$, $C_3F_6$, and $SF_6$.

9. The method according to claim 1, wherein the nanobubble lasts for 25 minutes~30 minutes.

10. The method according to claim 1, wherein the nanobubble has an application selected from the group consisting of the following: ultrasound contrast agent, drug carrier, gene carrier, clinical diagnosis and clinical therapy.

* * * * *